(12) United States Patent
Nelson et al.

(10) Patent No.: US 6,762,032 B1
(45) Date of Patent: Jul. 13, 2004

(54) COMPOSITIONS, ASSAY KITS, AND METHODS FOR USE RELATED TO A DISEASE CONDITION COMPRISING MULTIPLE SCLEROSIS AND/OR A PRO-MS IMMUNE RESPONSE

(75) Inventors: M. Bud Nelson, Worthington, OH (US); Emilio Barbera-Guillem, Powell, OH (US)

(73) Assignee: BioCrystal, Ltd., Westerville, OH (US)

( * ) Notice: Subject to any disclaimer, the term of this patent is extended or adjusted under 35 U.S.C. 154(b) by 0 days.

(21) Appl. No.: 09/643,277

(22) Filed: Aug. 22, 2000

Related U.S. Application Data

(60) Provisional application No. 60/207,577, filed on May 26, 2000, provisional application No. 60/151,999, filed on Sep. 1, 1999, and provisional application No. 60/150,256, filed on Aug. 23, 1999.

(51) Int. Cl.⁷ ..................... G01N 33/543; G01N 33/564
(52) U.S. Cl. ..................... 435/7.21; 435/7.23; 435/7.8; 435/7.94; 435/7.95; 436/506; 436/518; 436/813; 436/827
(58) Field of Search ............................. 435/7.21, 7.94, 435/7.95, 7.23, 7.8; 436/506, 518, 827, 813

(56) References Cited

U.S. PATENT DOCUMENTS

| | | | | |
|---|---|---|---|---|
| 5,011,920 A | * | 4/1991 | Hakomori et al. | 536/53 |
| 5,173,420 A | * | 12/1992 | Kannagi et al. | 435/240.27 |
| 5,192,662 A | * | 3/1993 | Shimada et al. | 435/7.23 |
| 5,194,385 A | * | 3/1993 | Yamashima | 435/240.27 |
| 6,080,554 A | | 6/2000 | Campine et al. | 435/7.1 |
| 6,383,740 B2 | * | 5/2002 | Collins | 435/5 |
| 6,599,756 B1 | * | 7/2003 | Robichaud et al. | 436/518 |
| 2003/0049692 A1 | * | 3/2003 | Latov et al. | 435/7.9 |
| 2003/0068664 A1 | * | 4/2003 | Albitar et al. | 435/7.92 |

OTHER PUBLICATIONS

Sadatipour et al., 1998, Increased circulating antiganglioside antibodies in primary and secondary progressive multiple sclerosis, Annals of Neurology, 44:980–983.

Acarin et al., 1996, Different antiganglioside antibody pattern between relapsing–remitting and progressive multiple sclerosis, Acta Neurol. Scand., 93:99–103.

Barbera–Guillem et al., 1999, Promotion of tumor invasion by cooperation of granulocytes and macrophages activated by anti–tumor antibodies, Neoplasia, 1:453–460.

* cited by examiner

*Primary Examiner*—David Saunders
(74) *Attorney, Agent, or Firm*—Benesch, Friedlander, Coplan & Aronoff LLP

(57) ABSTRACT

Provided are methods, and assay kits, and compositions useful for generating an indicator of a disease condition selected from the group consisting of multiple sclerosis (MS), a pro-MS immune response, and a combination thereof. A method for assaying a sample of an individual for an indicator of the disease condition comprises contacting the sample with a combination of two or more affinity ligands, at least one of which comprises a detection reagent; measuring an amount of the detection reagent which is bound to the sample in determining a value of a marker in the sample; wherein a difference in the value of the marker determined in the sample, when compared to the reference value, comprises an indicator of the presence of the disease condition.

44 Claims, 8 Drawing Sheets

COMPOSITIONS, ASSAY KITS, AND METHODS FOR USE RELATED TO A DISEASE CONDITION COMPRISING MULTIPLE SCLEROSIS AND/OR A PRO-MS IMMUNE RESPONSE

This application is a nonprovisional application based on earlier co-pending provisional applications Serial Nos. 60/150,256 filed Aug. 23, 1999, 60/151,999 filed Sep. 1, 1999, and 60/207,577 filed May 26, 2000, the disclosures of which are herein incorporated by reference.

FIELD OF THE INVENTION

The field of this invention is a disease condition selected from the group consisting of multiple sclerosis (including the various forms and stages of multiple sclerosis), a humoral immune response that may accompany multiple sclerosis (a "pro-MS immune response"), and a combination thereof.

BACKGROUND OF THE INVENTION

Multiple sclerosis ("MS") is a chronic inflammatory disease of the central nervous system. The characteristic pathological feature, and still used as the primary basis for diagnosis of MS, is demyelination of the myelin sheath of neurons in the central nervous system. MS affects 250,000 to 350,000 in the United States, and approximately 1 million people worldwide. Typically, MS begins as a relapsing-remitting disease (RRMS) with periodic episodes of associated symptoms (e.g. various forms of neuritis). Often RRMS eventually changes to a progressive course of disease, secondary progressive MS (SPMS), characterized by more inflammation than RRMS or primary progressive MS, and hence, more CNS tissue damage which results in more debilitating symptoms. However, in 10 to 20% of individuals, the disease initially develops in a progressive form known as primary progressive MS (PPMS).

There is clear understanding of the immunopathogenic processes associated with MS; and, to date, their lacks evidence of a unique immunologic abnormality in individuals with MS (Whitaker, 1998, N. Engl. J. Med. 339:339–340; Rudick et al., 1997, N. Engl. J. Med. 337:1604–1611). Because of the incomplete understanding of the pathogenesis of MS, therapeutic advances have been slow to emerge. The myelin sheath and oligodendrocytes are believed to be main targets of autoreactive T cells which, when activated and reach the central nervous system (CNS), are thought to secrete proinflammatory cytokines. These cytokines are believed to induce astrocytes and leukocytes (including by activating microglia and macrophages) to secrete enzymes which damage myelin, and result in inflammation, demyelination, and axonal damage in the central nervous system characteristic in MS. Thus, studies have implicated a cell-mediated immune response, involving T cells recognizing epitopes of myelin basic protein (MBP), in the pathogenesis of MS.

Currently, the characterization of disease condition related to MS (including diagnosis, staging, monitoring disease progression, monitoring treatment effects on disease activity, and the like) is imprecise. Imaging that detects what appears to be plaques in CNS tissue is typically insufficient, by itself, to give a definitive diagnosis of MS. Often, diagnosis of MS is made only after both detection of plaques and of clinically evident neuropathy. It is clear that diagnosis of MS is usually made well after initiation of the disease process; i.e., only after detection of a sufficient number of plaques and of clinically evident neurological symptoms. Additionally, staging of MS is typically done by subjective measurements of exacerbation of symptoms, as well of other clinical manifestations. There are difficulties in diagnosis and staging because symptoms vary widely among individuals and change frequently within the individual. Thus, there is the need for tests which can aid in the diagnosis and staging of MS. Further, presently there are no commercially available tests to evaluate for the presence of a pro-MS immune response. There is a need for laboratory tests that distinguish individuals who are more likely to have a favorable prognosis (e.g., one or more of stable remission; limited, localized disease progression; response to anti-MS therapy that either stabilizes or reduces the rate of disease progression) from individuals who are likely to have an unfavorable prognosis (e.g., individuals having undergone anti-MS therapy but who still have indications of a pro-MS immune response, and are thus still at risk for progression of the disease process; individuals having both clinically evident MS and a pro-MS immune response). Additionally, there is a need for markers that can be used as indicators for predicting whether a particular therapeutic (e.g., drug or immunotherapeutic) can effectively reduce a pro-MS immune response. Recently, one skilled in the field of MS summarized the need: "The need for reliable markers of disease activity in multiple sclerosis (MS) to better guide basic research, diagnosis, treatment, and monitoring of therapy is well-recognized."

Therefore, a need exists for compositions and methods which may be used to characterize a disease condition selected from the group consisting of MS, a pro-MS immune response, and a combination thereof.

SUMMARY OF THE INVENTION

It is suggested that MS may actually be different diseases of similar pathology which are lumped together. According to a primary object of the present invention, provided are markers which may be determined by analyzing a body fluid of an individual having a disease condition selected from the group consisting of MS, a pro-MS immune response, and a combination thereof; wherein the markers differ in the disease condition as compared to reference values for the respective markers established from apparently healthy individuals.

In another object, one or more markers may be an indicator for a form or forms of the disease condition; may also be used to stage the development or progression of the disease condition; and may be used to monitor treatment of the disease condition.

In another object, provided are methods for assaying a clinical sample for the one or more markers. Also provided are assay kits for use in detecting or detecting and quantitating (individually or collectively referred to hereinafter as determining) an amount of the one or more markers in practicing the methods according to the present invention.

In another object provided are detection of sialocomplexes, and methods of removing sialocomplexes from a body fluid of an individual having a disease condition selected from the group consisting of MS, a pro-MS immune response, and a combination thereof.

The above and other objects, features, and advantages of the present invention will be apparent in the following Detailed Description of the Invention, when read in conjunction with the accompanying drawings.

DETAILED DESCRIPTION OF THE INVENTION

Definitions

Figure 1:
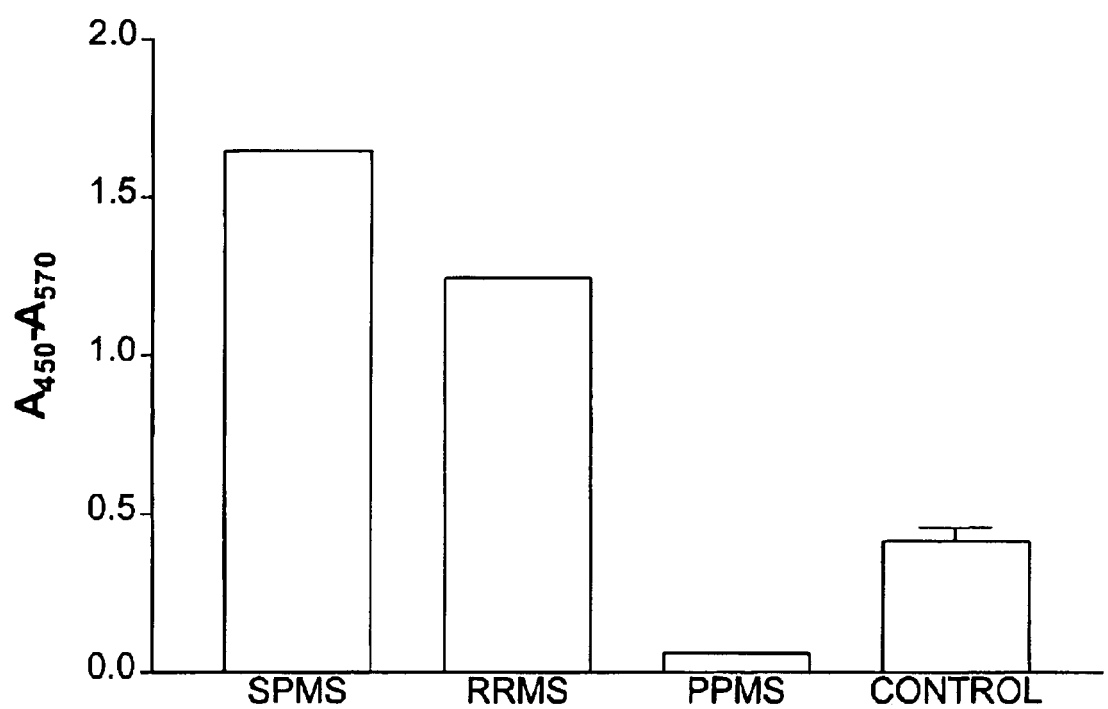
FIG. 1 is a graph illustrating the use of a combination of affinity ligands comprising anti-α(2,6)NeuAc Ab and anti-human IgG to generate an indicator for a disease condition selected from the group consisting of MS, a pro-MS immune response, and a combination thereof.

The term "sialocomplexes" is used herein, for purposes of the specification and claims, to mean one or more complexes found in the body fluid of an individual having a disease condition selected from the group consisting of MS, a pro-MS immune response, and a combination thereof; wherein a complex comprises a combination of molecules which are bound to one another due to the binding specificity of at least one of the molecules; and wherein the molecules comprise a combination of two or more molecules selected from the group of molecules consisting of a glycolipid having at least one terminal, alpha 2,6-linked sialic acid, a member of the sialoadhesin family (also know as siglec family), and a human antibody which specifically binds an epitope comprising a terminal, alpha 2,6-linked sialic acid. In a preferred embodiment, the human antibody is selected from the group consisting of IgG, IgM, and a combination thereof. The terminal, alpha 2,6-linked sialic acid comprises a terminal sialic acid alpha 2,6-linked to galactose (Gal) or a terminal sialic acid alpha 2,6-linked to N-acetyl galactosamine (GalNAc). Members of the sialoadhesin family are known to those skilled in the art to comprise: CD22 (Siglec-2) having binding specificity for terminal, alpha 2,6-linked sialic acids (alpha 2,6-linked to either Gal or GalNAc); myelin-associated glycoprotein ("MAG", Siglec-4) having binding specificity for a terminal fi alpha 2,3-linked sialic acid (alpha 2,3-linked to Gal); CD33 (Siglec-3) having binding specificity for alpha 2,3-linked sialic acids, with a lesser degree of binding to alpha 2,6-linked sialic acids; sialoadhesin ("Sn"; Siglec-1) having binding specificity for terminal alpha 2,3-linked or terminal alpha 2,8-linked sialic acids; OB-BP2 (Siglec-5) having binding specificity for alpha 2,3-linked sialic acids, with a lesser degree of binding to alpha 2,6-linked sialic acids; and OB-BP1 (Siglec-6) having binding specificity for terminal, alpha 2,6-linked sialic acids (alpha 2,6-linked to GalNAc). The glycolipid comprises a ganglioside having at least one terminal alpha 2,6-linked sialic acid. In a preferred embodiment, the glycolipid comprises at least one terminal alpha 2,6-linked sialic acid which comprises a sialic acid selected from the group consisting of sTn antigen (a terminal sialic acid which is alpha 2,6-linked to GalNAc), a terminal sialic acid which is alpha 2,6-linked to Gal, or a combination thereof (when there is more than one terminal, alpha 2,6-linked sialic acid). The glycolipid may further comprise one or more of a terminal alpha 2,3-linked sialic acid, and a terminal alpha 2,8-linked sialic acid. Such glycolipids are known to included, but are not limited to, one or more of the alpha series of gangliosides (e.g., GD1αa, GT1aα, GQ1bα, derivatives thereof which contain one or more additional terminal sialic acids alpha 2,6 linked to GalNAc, and a combination thereof) Such derivatives may comprise one or more of the following structures:

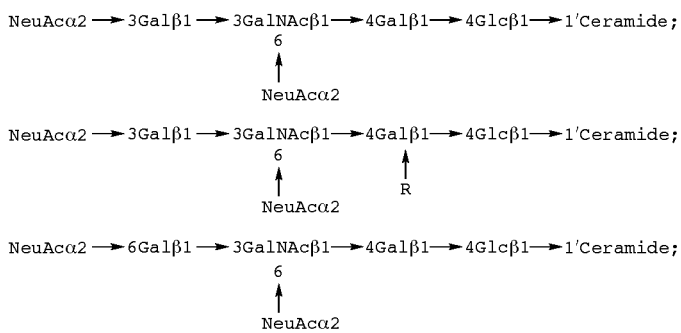

-continued

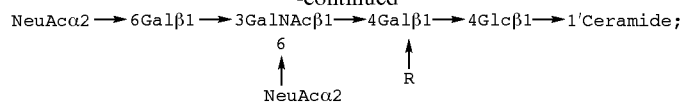

wherein R is selected from the group consisting of one sialic acid, or two sialic acids linked together. For example, R may comprise a 2,3-linked sialic acid or a 2,6-linked sialic acid; R may comprise two sialic acid residues linked together (e.g., a sialic acid which is 2,8-linked to a sialic acid which is 2,3-linked to a Gal). In a preferred embodiment of the present invention, the glycolid is produced in a greater amount and shed from CNS tissue which is damaged from or affected by a chronic inflammatory reaction as a result of a pro-MS immune response and/or a T cell-mediated response, as compared to an amount produced and shed by CNS tissue which is not undergoing a chronic inflammatory response. Thus, in a preferred embodiment wherein the sialocomplexes comprise a glycolipid, the sialocomplexes further comprise one or more members of the sialoadhesin family which specifically binds to a terminal sialic acid of the glycolipid. In another preferred embodiment, wherein the sialocomplexes comprise a glycolipid, the sialocomplexes further comprise a human antibody which specifically binds a terminal, alpha 2,6-linked sialic acid of the glycolipid ("anti-α(2,6)NeuAc Ab") and may further comprise one or more members of the sialoadhesin family which specifically binds to a terminal sialic acid of the glycolipid. More preferably, the anti-α(2,6)NeuAc Ab comprises an anti-sTn Ab. For example, wherein the sialocomplexes comprise a terminal sTn available for binding, the one or more molecules complexed to sTn may be selected from the group consisting of anti-sTn Ab, a member of the sialoadhesin which binds specifically to sTn (e.g., CD22), and a combination thereof. In a preferred embodiment, sialocomplexes are comprised of glycolipid comprising at least one terminal alpha 2,6-linked sialic acid and a terminal alpha 2,3-linked sialic acid, and one or more molecules complexed to a terminal sialic acid of the qlycolipid component of the sialocomplexes. The one or more molecules may be selected from the group consisting of a molecule complexed to the terminal alpha 2,6-linked sialic acid of the glycolipid (e.g., anti-α(2,6)NeuAc Ab, CD22, or a combination thereof), a molecule complexed to the terminal alpha 2,3-linked sialic acid of the glycolipid (e.g., MAG, CD33 sialoadhesin, or a combination thereof), and a combination thereof. If the glycolipid further comprises a terminal alpha 2,8-linked sialic acid, a molecule which may be complexed to the terminal alpha 2,8-linked sialic acid may be sialoadhesin. In another preferred embodiment, the sialocomplexes comprise immune complexes comprised of the glycolipid, and human anti-sTn Ab. In another preferred embodiment, the sialocomplexes comprise glycolipid, human anti-sTn Ab, and at least one member of the sialoadhesin family selected from the group consisting of CD22, MAG, CD33, sialoadhesin, and a combination thereof. It will be apparent to one skilled in the art that sialocomplexes may comprise a single population of complexed molecules, or may comprise a mixed (regarding components of the complexes) population of complexed molecules. As an illustrative, non-limiting example, the sialocomplexes may comprise a single population of immune complexes comprised of glycolipid complexed to human anti-sTn Ab. In another illustrative, non-limiting example, the sialocomplexes may comprise a mixed population of sialocomplexes with each population differing in their composition of components; e.g., sialocomplexes comprised of glycolipid complexed to MAG and anti-α(2,6)NeuAc Ab, and sialocomplexes comprised of glycolipid complexed to CD22 and anti-α(2,6)NeuAc Ab.

The term "affinity ligand" is used herein, for purposes of the specification and claims, to mean a molecule which has binding specificity and avidity for a component of sialocomplexes or of the sample being analyzed, wherein the component is selected from the group consisting of a member of the sialoadhesin family, a glycolipid, and an antibody which is specifically bound to the sialocomplex (e.g., anti-α(2,6)NeuAc Ab). In a preferred embodiment, the affinity ligand may be selected from the group consisting of a monoclonal antibody having binding specificity for a sialoadhesin family member (for binding a component comprising a sialoadhesin family member, anti-α(2,6)NeuAc Ab (for binding epitope on a component wherein the epitope comprises a free terminal alpha 2,6-linked sialic acid), anti-human antibody (e.g., anti-human IgG or anti-human IgM, for binding a component comprising human anti-α(2,6)NeuAc Ab), and a combination thereof (e.g., a combination of affinity ligands, each having binding specificity for a component). For instance, where sialocomplexes comprise a glycolipid complexed to MAG, the affinity ligand may be selected from the group consisting of anti-MAG monoclonal antibody (mAb), anti-sTn mAb, and a combination thereof. In another preferred embodiment, where sialocomplexes comprise glycolipid complexed to antibody having binding specificity for the glycolipid, the affinity ligand may be selected from the group consisting of anti-sTn Ab (for binding free sTn epitope of glycolipid in the sialocomplexes), anti-human antibody (e.g., anti-human IgG or IgM) (for binding the antibody component of the sialocomplexes), and a combination thereof. A preferred affinity ligand may be used to the exclusion of affinity ligands other than the preferred affinity ligand.

It will be apparent to one skilled in the art that the nature of the affinity ligand may depend on the component of the sialocomplexes for which it has binding specificity. As known to those skilled in the art, affinity ligands may include, but are not limited to, lectins, antibodies (including immunoreactive fragments produced or derivatives derived from antibodies), peptides, and aptamers. Commercially available lectins that may have binding specificity for a terminal sialic acid may include, but are not limited to, Sambucus nigra lectin (e.g., for alpha 2,6-linked), sialic acid-binding lectin of Helicobacter pylori (e.g., for alpha 2,6-linked) and Maackia Amurensis agglutinin (e.g., for alpha 2,3-linked). Commercially available monoclonal antibodies that may have binding specificity for the glycolipid may comprise anti-sTn Abs including, but not limited to, mAb B72.3, and mAb HBSTn; or monoclonal antibodies having binding specificity for an epitope comprising a terminal sialic acid which is alpha 2,6-linked to galactose. Monoclonal antibodies may comprise immunoreactive fragments produced or derivatives derived from an antibody molecule, which fragments retain binding function so as to be able to bind the antigen sufficiently for use in immunoassays. Such fragments are known to those skilled in the art to include $F(ab')_2$, Fab', Fab, Fv, scFV, Fd' and Fd fragments.

Methods for producing the various fragments from MAbs are well known in the art (see, e.g., Plückthum, 1992, *Immunol. Rev.* 130: 152–188). For example, F(ab')$_2$ can be produced by pepsin digestion of the monoclonal antibody, and Fab' may be produced by reducing the disulfide bridges of F(ab')$_2$fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. Aptamers can be made using methods described in U.S. Pat. No. 5,789,157 (herein incorporated by reference). An affinity ligand may further comprise a detectable moiety which has been coupled to the affinity ligand using covalent or noncovalent or other means known in the art. The term "detectable moiety" is used herein, for purposes of the specification and claims, to mean a label molecule that is directly (e.g., signal-generating) or indirectly detectable. For example, detection and quantitation of the detectable moiety (as part of the affinity ligand, and when the affinity ligand is specifically bound to sialocomplexes according to the present invention) may be correlative of an amount of sialocomplexes present in a sample being analyzed. Detectable moieties may include, but are not limited to, one or more of dyes, enzymes (e.g., peroxidase, alkaline phosphatase, etc.), radioisotopes, haptens (e.g., biotin, avidin, etc.), chromophores, luminescent molecules, fluorescent molecules, fluorescent nanocrystals, as known to those skilled in the art of diagnostics. When the detectable moiety comprises an enzyme, various substrates may be employed to provide a detectable signal such as color, light absorption, fluorescence, chemiluminescence, or the like. The particular detectable moiety is not critical to the invention, and is primarily a matter of choice and sensitivity; and may further be dependent upon the immunoassay format utilized or detection system utilized. Where an affinity ligand is not labeled with a detectable moiety, a secondary affinity ligand having a signal-generating detectable moiety may be used to specifically bind the affinity ligand (e.g., a combination of primary antibody, and labeled secondary antibody), as known to those skilled in the art.

The term "sample" is used herein, for purposes of the specification and claims, to mean a body fluid in which sialocomplexes may be found, or which may be analyzed for the markers according to the present invention. Such body fluids may comprise blood, urine, lymph, cerebrospinal fluid (CSF), or an effusion associated with multiple sclerosis. The term "sample" also encompasses a preparation which is derived from the body fluid (e.g., plasma or serum are each derived from blood).

The term "immunoassay" is used herein, for purposes of the specification and claims, to mean an assay format that may be used to determine an amount of sialocomplexes according to the present invention in a sample, or in which a combination of affinity ligands may be used in the analysis of a sample to generate one or markers which may comprise an indicator of a disease condition selected from the group consisting of MS, a pro-MS immune response, and a combination thereof. The immunoassay may be qualitative (detecting the presence or absence) or quantitative (detection in a manner that allows quantitation of the amount); e.g., in determining an amount of sialocomplexes according to the present invention. As appreciated by those skilled in the art, various formats of immunoassays may be used in the analysis of a sample. Factors which influence which format is utilized may include, but is not limited to, the affinity ligands utilized, the components being assayed for, sensitivity of the determination, and preference of the user of the format. In principle, conventional immunoassays known to those skilled in the art may have a suitable format which may be utilized in the methods according to the present invention. Such immunoassay formats are known to those skilled in the art to include, but are not limited to, an inhibition-type immunoassay, a competitive immunoassay, an interference immunoassay, an enzyme-linked immunosorbent assay (ELISA), a competitive ELISA, a sandwich immunoassay, a solid phase immunoassay, heterogeneous competitive immunoassay (liquid phase is separated from the solid phase), a kinetic immunoassay, a precipitation immunoassay, an agglutination immunoassay, an enzyme immunoassay, a fluorescence immunoassay, a radioimmunoassay, a liquid phase immunoassay, and other immunoassays.

The terms "differs" and "difference" is used herein relative to a comparison between one or more markers or amounts determined from a sample and that of a comparative value (reference value or baseline value), for purposes of the specification and claims, to mean that the markers (e.g., amount of sialocomplexes, or pattern of immunoreactivity when the sample is analyzed) determined in a sample falls outside the comparative value (e.g., outside a range of normal clinical values for the indicator that is established by clinical studies of apparently healthy individuals, the range of normal clinical values being referred to as a "reference value"). Hence, where a marker determined according to the present invention differs with respect to a reference value, the marker may comprise an indicator for a disease condition selected from the group consisting of MS, a pro-MS immune response, and a combination thereof. In a preferred use, the term "differs" is used herein, for purposes of the specification and claims, to mean that there is a statistically significant difference between a marker determined according to the present invention from a clinical sample, and a comparative value for the marker selected from the group consisting of a reference value (comprising a predetermined value or a range of values in the same type of body fluid of apparently healthy individuals), a baseline value (comprising a predetermined value from one or more previous samples of the same type of body fluid obtained from the same individual being tested), and a combination thereof. In a preferred embodiment, a statistically significant difference between a first value and a second value in a comparison may comprise the first value being at least about two standard deviations outside the mean of the second value. In general, the methods, assay formats, and compositions, of the present invention are used to generate indicators for a disease condition selected from the group consisting of MS, a pro-MS immune response, and a combination thereof; in providing an additional parameter to a competent health professional in making a medical opinion.

The term "pro-MS immune response" is used herein for purposes of the specification and claims, to mean a humoral immune response induced against an epitope comprising a terminal alpha 2,6-linked sialic acid (e.g., comprising sialyl Tn or sTn which comprises a terminal sialic acid alpha 2,6-linked to GalNac) of a shed antigen (glyco-molecule), resulting in production of IgG antibody against the epitope ("anti-α(2,6)NeuAc Ab"), and complexes comprised of the shed antigen comprising the epitope complexed to anti-α(2, 6)NeaAc Ab, and may further comprise one or more members of the sialoadhesin family; wherein the shed antigen is released or produced particularly in relation to CNS tissue damage characteristic of MS during the MS disease process. In a preferred embodiment, the resultant complexes bind to and induce Fc receptor-expressing cells (e.g., one or more cell types selected from the group consisting of granulocytes, macrophages, microglia, activated mast cells, astrocytes, oligodendrocytes) which results in the release of inflammatory mediators (e.g., cytokines and/or tissue degradative enzymes) which may promote (contribute to) CNS tissue damage characteristic of MS (e.g., demyelination and plaques characteristic of MS). A similar immune response, a pro-tumor response, has been described in commonly owned U.S. Pat. No. 6.251,616 (the disclosure of which is herein incorporated by reference). In a preferred embodiment, the anti-α(2,6) NeuAc Ab is induced by a shed antigen comprising glycolipid, as previously described herein in more detail. Cellular markers for a pro-MS immune response have been described in detail in U.S. application Ser. No. 60/150256, now abandoned, the disclosure of which is herein incorporated by reference.

The term "biological assay conditions" is used herein, for purposes of the specification and claims, to mean those conditions under which an affinity ligand can specifically bind to the molecule for which it has binding specificity (e.g., a component of the sialocomplexes according to the present invention). As known to those skilled in the art, such conditions may include one or more of: a pH range of from about 5 to 9, ionic strengths such as that ranging from distilled water to about 1 molar sodium chloride, and a temperature in the range of from about 4° C. to about 45° C.; and may further include a time sufficient for binding to occur (e.g., in a range of from about 10 minutes to about 2 hours).

There is a need for clinical tests which can aid in the diagnosis of MS. Additionally, there is a need for clinical tests which can detect one or more of: individuals at risk of developing MS, initiation of inflammatory processes preceding development of a pattern of clinical symptoms characteristic of MS, detection of MS at an earlier point in time than currently available techniques, and monitoring the progression of MS (e.g., from RRMS to SPMS). Further, presently there are no commercially available tests to evaluate for the presence of a pro-MS immune response. There is a need for laboratory tests that distinguish individuals who are more likely to have a favorable prognosis (e.g., one or more of stable remission; limited, localized disease progression; response to anti-MS therapy that either stabilizes or reduces the rate of disease progression) from individuals who are likely to have an unfavorable prognosis (e.g., individuals having undergone anti-MS therapy but who still have indications of a pro-MS immune response, and are at risk for progression; individuals having both clinically evident MS and a pro-MS immune response). Additionally, there is a need indicators for predicting whether a particular therapeutic (e.g., drug or immunotherapeutic) can effectively reduce a disease process comprising MS and/or a pro-MS immune response.

The present invention provides a method for analyzing a sample from an individual being screened for, or suspected of having, or known to have a disease condition selected from the group consisting of MS, a pro-MS immune response, and a combination thereof. The method of the present invention is achieved because of a discovery that a combination of affinity ligands can be used in an immunoassay to generate one or more indicators that appear to differ in individuals having a disease condition selected from the group consisting of MS, a pro-MS immune response, and a combination thereof, as compared to a comparative values determined from healthy controls or in individuals having inflammatory diseases other than MS. As will be apparent from the following descriptions, the methods and assay kits according to the present invention may be used to confirm a suspicion of MS (based on either initial symptoms or other clinical evidence initially presented), to determine the state of the disease condition in the individual, to monitor the course of the disease condition (e.g., progression; or regression after treatment), and the like. A marker determined according to the present invention may be used individually or in a panel of markers for detecting a disease condition; i.e., to distinguish between primary progressive MS, relaxing remitting MS, and secondary progressive MS, and to detect the presence or absence of a pro-MS immune response. For example, to determine the disease condition, the observed values for the markers determined from analysis of the clinical sample are compared to reference values, wherein the markers comprise indicators which are correlated to a disease condition or form thereof. A marker determined according to the present invention may be used individually or in a panel of markers for staging the disease condition; i.e., to distinguish between relaxing remitting MS, and secondary progressive MS. For example, to determine the stage of the disease condition, the observed values for the markers determined from analysis of the clinical sample are compared to reference values, wherein the markers comprise indicators which are correlated to a stage of a disease condition. A marker determined according to the present invention may be used individually or in a panel of markers for staging the disease condition; i.e., to distinguish between relaxing remitting MS, and secondary progressive MS. For example, to determine the stage of the disease condition, the observed values for the markers determined from analysis of the clinical sample are compared to comparative values, wherein when the observed values of the markers differ from the respective comparative values, the markers comprise indicators which are correlated to a stage of a disease condition. A marker determined according to the present invention may be used individually or in a panel of markers for monitoring the course of the disease condition; i.e., whether the disease condition is progressing (e.g., worsening, and therefore predictive of a worsening in symptoms or severity) in course, or has stabilized, or has improved by regression (e.g., a change in the one or markers to within or closer to the range of the comparative values). For example, to determine the course of the disease condition, the observed values for the markers determined from analysis of the clinical sample are compared to comparative values, wherein when the observed values of the markers differ from the respective comparative values, the markers comprise indicators which are correlated to the course of a disease condition.

Assay kits are provided for performing the above described methods. In one embodiment, the assay kit comprises a combination of affinity ligands comprising an anti-human Ab; at least one affinity ligand having binding specificity for a member of the sialoadhesin family; and an affinity ligand having binding specificity for an epitope comprising a terminal alpha 2,6-linked sialic acid. The sample may be assayed using a combination of the affinity ligands in determining one or more markers or an amount of sialocomplexes according to the present invention. One or more affinity ligands of the combination of affinity ligands may further comprise a detectable moiety (in comprising a "detection reagent"). In a preferred embodiment, the anti-human antibody is selected from the group consisting of an anti-human IgG mAb, an anti-human IgM mAb, and a combination thereof. In a preferred embodiment, the affinity ligand having binding specificity for an epitope comprising a terminal alpha 2,6-linked sialic acid comprises an anti-sTn mAb. In another embodiment, the assay kits may include various components, depending on the complexity of the screening method utilized for determining an amount of sialocomplexes according to the present invention. Assay kits may further comprise one or more reagents comprising a reference standard comprising a known amount of the one or more markers (e.g., the sialocomplexes) desired to be detected in the assay, instructions for use of the assay kit and components, and optionally, other accessories useful in carrying out the methods of the present invention.

A method according to the present invention may be performed in a liquid phase or a solid phase of an immunoassay. In a preferred immunoassay format for assaying a clinical sample in a method according to the present invention, the immunoassay comprises: affinity ligand, having binding specificity for a component of the sialocomplexes, which is immobilized to a support surface in forming a solid phase ("immobilized affinity ligand"); contacting and reacting the solid phase with a sample under biological assay condition sufficient for sialocomplexes that may be present in the sample to be specifically bound by the immobilized affinity ligand; and then determining an amount of sialocomplexes bound to the immobilized affinity ligand. In a preferred embodiment, determining an amount of sialocomplexes bound to the immobilized affinity ligand may be accomplished by contacting and reacting the solid phase containing the sample under biological assay conditions with one or more affinity ligands having binding specificity for the sialocomplexes (e.g., components thereof) for detecting the sialocomplexes (the affinity ligand comprising a "detection reagent"), and then measuring the amount of the detection reagent which remains bound to the solid phase (e.g., by measuring the amount of signal generated by the detectable moiety portion of the detection reagent), wherein the amount of the bound detection reagent is measured and correlated to the amount of sialocomplexes in the sample.

In this preferred embodiment, the affinity ligand is immobilized onto a solid phase. As known to those skilled in the art, a solid phase may comprise a solid support that may include, but is not limited to, a bead (e.g., polystyrene, paramagnetic, etc.), test tube, reaction vessel other than a test tube, reaction chamber, microtiter plate well, dipstick, slot for performing reactions therein (e.g., of a microarray), a sheet for performing reactions thereon (e.g., nitrocellulose or derivatized sheet material), slides, films, membranes, or the like. The particular solid phase is not critical, and any solid phase suitable for an immunoassay may be used; e.g., where non-specific binding may be minimized, and where the solid phase is suitable for use in a convenient protocol without significantly interfering with measurement of an amount of an analyte such as sialocomplexes. The affinity ligand may be immobilized to the solid phase using covalent or noncovalent means as known to those skilled in the art. Such means will depend on factors including the chemical nature of the affinity ligand, and the nature of surface of the solid support used in forming the solid phase. The particular manner in which the affinity molecule is immobilized is not critical so long as it is compatible with the intended purpose of an immunoassay, and with the methods according to the present invention and the reagents used therein. For example, where the affinity ligand is a protein such as a lectin or antibody, the affinity ligand is adsorbed onto a solid surface in forming a solid phase. Techniques for coating affinity ligands onto solid surfaces are well known in the art. Typically, after immobilizing the affinity ligand, the solid phase is then treated to reduce non-specific binding to any subsequent reactants added to the solid phase. More particularly, non-specific binding sites on the solid phase (i.e., those sites not occupied by affinity ligand) are generally blocked using blocking agents alone, or in conjunction with a detergent (the latter reduces non-specific binding). Preferred blocking agents are known to those skilled in the art to include, but are not limited to, milk, bovine serum albumin, casein, gelatin, and betaglobin. Detergents include non.-interfering concentrations of Tween, NP40, and the like.

After preparing the solid phase, the sample (e.g., portion or aliquot of the sample) may be added to and contacted with the solid phase and reacted under biological assay conditions sufficient for sialocomplexes, if present in the sample, to be bound by the immobilized affinity ligand of the solid phase. It may be desirable to add to separately assayable solid phases one or more reference standards comprising a known amount of the sialocomplexes to be measured so as to aid in interpreting the results of the assay (e.g., to ensure that the affinity ligands used still maintain their binding ability). After such incubation, the solid phase may be washed so as to remove from the solid phase any unbound or non-specifically bound contents of the sample. Generally, one to several washes with a solution compatible with the immunoassay will be sufficient to wash the unbound or non-specifically bound contents from the solid phase. After washing, a solution containing the detection reagent may be added to and contacted with the solid phase. Generally, the detection reagent should be added in a concentration that is sufficient to saturate all or substantially all sialocomplexes that may be bound to immobilized affinity ligand in the solid phase; and reacted under biological assay conditions sufficient for the detection reagent to contact and bind sialocomplexes that may be present in the solid phase. Typically, after incubation, the solid phase is washed to remove any unbound or non-specifically bound detection reagent. After the wash, detectable signal, generated from the detectable moiety of the detection reagent, that may be bound sialocomplexes in the solid phase, is detected by means conventional for the immunoassay format being utilized. Measurement of bound detection reagent may be used to quantitatively or qualitatively determine an amount of sialocomplexes in the sample. For quantitative analysis, units of measurement may be computed, such as through use of an absorbance value calculated for the sample, as compared to absorbance values for reference standards that are run in parallel and as plotted on a standard curve. Depending on the type of detection reagent (affinity ligand and detectable moiety) used, and immunoassay format utilized, other units may be used to generate a measurement, such as optical density, or amount of fluorescent emission. Thus, an amount of sialocomplexes determined using an immunoassay may be expressed as a relative value (e.g., relative to means of measurement such as absorbance), or expressed as an actual value (e.g., in weight per volume). Accordingly, in a preferred method according to the present invention, the immunoassay comprises: a combination of affinity ligands comprising two affinity ligands selected from the group consisting of an anti-human Ab, an affinity ligand having binding specificity for a member of the sialoadhesin family, and an affinity ligand having binding specificity for an epitope comprising a terminal alpha 2,6-linked sialic acid; and wherein at least one of the affinity ligands comprises an immobilized affinity ligand, and at least one of the affinity ligands comprises a detection reagent for use in analyzing the sample in the solid phase.

In another preferred embodiment, provided is a method for analyzing a sample for markers associated with a a disease condition selected from the group consisting of MS, a pro-MS immune response, and a combination thereof. The method may use an immunoassay format essentially as described above. The clinical sample is added to and incubated with the immobilized affinity ligand under biological assay conditions. The one or more affinity ligands comprising the detection reagent is then added to the solid phase. Detection and measurement of the bound detection reagent in the solid phase containing the sample being analyzed results in a value that comprises a marker which may be compared to a comparative value, wherein where the value of the marker differs as compared to the comparative value, the marker comprises an indicator which may be correlated to a disease condition selected from the group consisting of MS, a pro-MS immune response, and a combination thereof.

EXAMPLE 1

This example illustrates use of a combination of affinity ligands to generate an indicator from analysis of a sample. Also, this example illustrates one embodiment of the present invention wherein an amount of sialocomplexes is determined in a sample by an immunoassay according to the present invention. In this illustrative example, the sample was analyzed by contact under biological assay conditions with a combination of affinity ligands comprising a murine anti-$\alpha$(2,6)NeuAc Ab for binding specifically to an epitope comprising free (unbound) terminal alpha 2,6-linked sialic acid, and an anti-human IgG antibody for binding specifically to a human antibody. In a preferred embodiment, the human antibody component being assayed for is an antibody having binding specificity for an epitope comprising sTn; and hence, determination of an amount of human antibody in the sample which differs from a reference value is an indicator of a disease condition selected from the group consisting of MS, a pro-MS immune response, and a combination thereof. To illustrate this embodiment, wells of a polystyrene microtiter plate (a solid phase) were coated with the murine anti-$\alpha$(2,6)NeuAc Ab comprising anti-sTn mAb as the immobilized affinity ligand by adding 100 $\mu$l/well of a 10 $\mu$g/ml solution diluted in phosphate buffered saline (PBS). The plate was incubated overnight at 40° C. The solution was then removed, and the wells were washed to remove any unbound mAb. The plates were then blocked with a blocking solution comprising 1% bovine serum albumin, 0.05% Tween, and 2% goat serum for 1 hour at room temperature, and then washed to remove excess blocking solution from the solid phase.

The samples reacted with the solid phase under biological assay conditions comprised plasma from: individuals with no apparent disease or pathology ("Reference Value"); individuals having relapsing-remitting (RRMS), or secondary progressive (SPMS), or primary progressive (PPMS) form of multiple sclerosis. The plasma was diluted with 1:50 with buffer (PBS+0.05% Tween) before addition to the solid phase. Aliquots of 100 $\mu$l were added to appropriately designated wells of the microtiter plate. The plate was then incubated for 1 hour at room temperature, and then washed with buffer to remove unbound or non-specifically bound plasma components from the solid phase. The affinity ligand comprising the detection reagent for assaying the sample comprised anti-human IgG labeled with peroxidase (e.g., horseradish peroxidase) for detecting antibody of the IgG class, if present, as a component of the sample bound to the solid phase. The detection reagent comprising anti-human IgG labeled with peroxidase was added- to the appropriately designated wells at the dilution recommended by the manufacturer. The plate was then incubated for 1 hour at room temperature, and then washed with buffer to remove unbound or non-specifically bound, labled anti-human IgG from the solid phase. Substrate, comprising tetramethyl benzidine (TMB) was then added to determine peroxidase activity of bound etection reagent, if present. Resultant color development was quantitated at 450 nanometers using a plate-reading spectrophotometer. FIG. 1 illustrates an amount selected from the group consisting of a marker comprising an observed level of immunoreactivity determined from the samples, and an amount of sialocomplexes determined from the samples, as measured by absorbance at 450 nm (with a correction at absorbance 570) and expressed as the mean absorbance.

As illustrated in FIG. 1, the observed value for a marker comprising human IgG and sTn epitope that may be present together in clinical samples from individuals with RRMS or with SPMS differs (is increased) as compared to the reference value (FIG. 1 "Control"). However, such an increase in this marker was not observed in clinical samples from an individual having a disease condition comprising PPMS, a slow progressing form of MS. These results suggest that (a) a pro-MS immune response, as identified by an increase (as compared to a reference value) in this marker, and which may represent sialocomplexes comprising IgG containing-immune complexes, may be present in individuals with RRMS, or with SPMS; (b) that this marker comprises an indicator that may be used to distinguish different forms of MS (e.g., PPMS lacks the indicator, and hence, may be distinguished from RRMS and SPMS); and (c) that a combination of affinity ligands comprising an affinity ligand having binding specificity for an epitope comprising sTn, and anti-human Ab (anti-human IgG), may be used to generate an indicator of a disease process selected from the group consisting of RRMS, SPMS, a pro-MS immune response, or a combination thereof (i.e., RRMS and a pro-MS immune response, or SPMS and a pro-MS immune response).

EXAMPLE 2

Figure 2A:
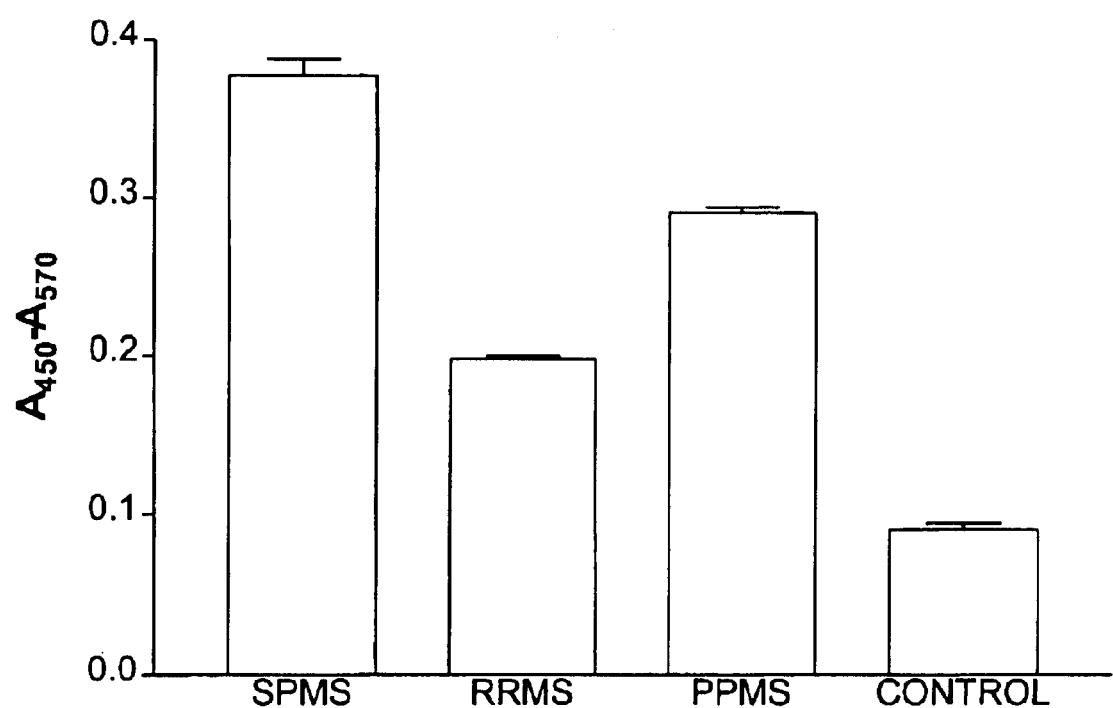
FIG. 2A is a graph illustrating the use of a combination of affinity ligands comprising anti-MAG mAb and anti-human IgM to generate an indicator for a disease condition selected from the group consisting of MS, a pro-MS immune response, and a combination thereof.
Figure 2B:
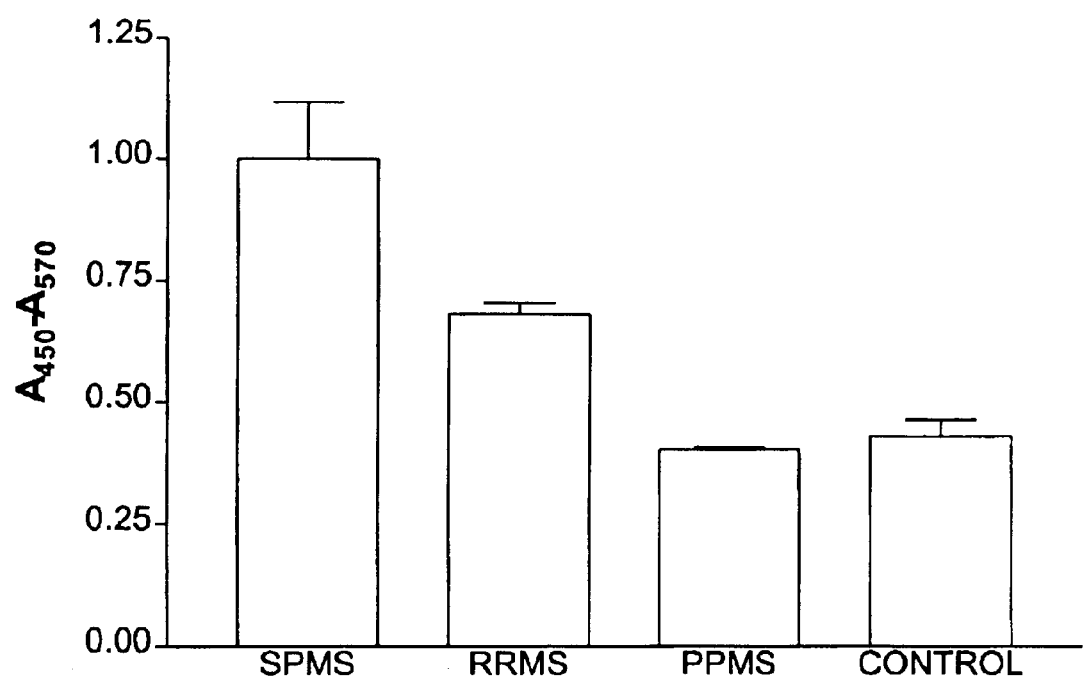
FIG. 2B is a graph illustrating the use of a combination of affinity ligands comprising anti-MAG mAb and anti-human IgG to generate an indicator for a disease condition selected from the group consisting of MS, a pro-MS immune response, and a combination thereof.
Figure 2C:
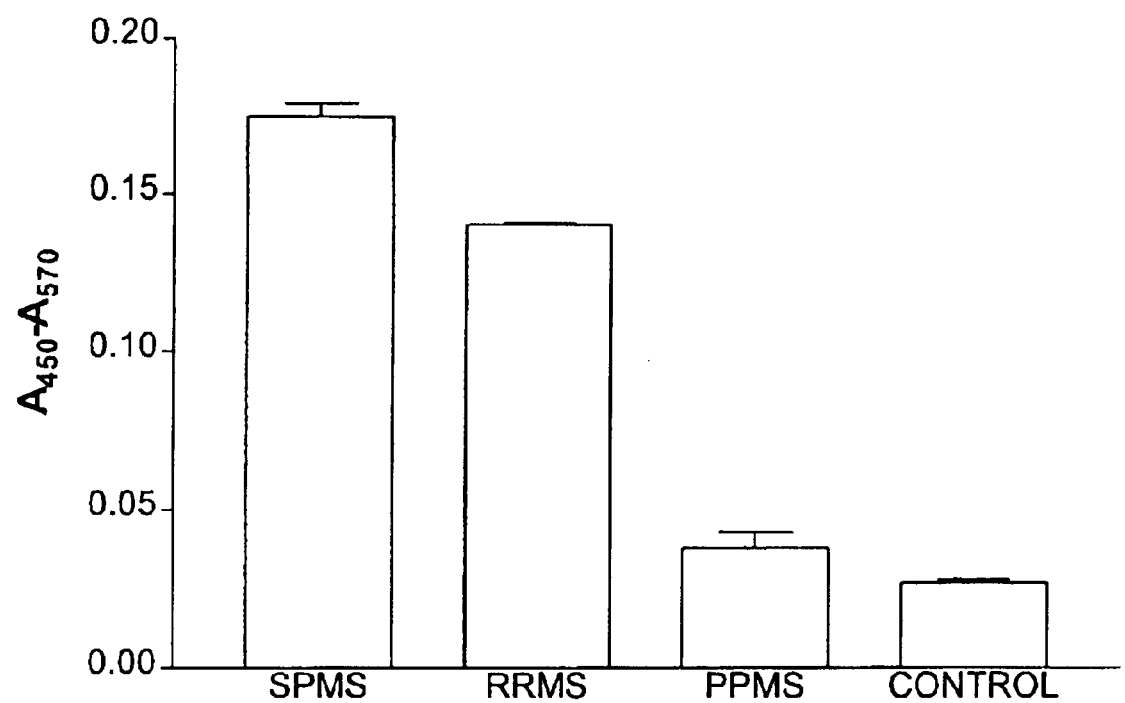
FIG. 2C is a graph illustrating the use of a combination of affinity ligands comprising anti-MAG mAb and anti-sTn mAb to generate an indicator for a disease condition selected from the group consisting of MS, a pro-MS immune response, and a combination thereof.

This example illustrates another embodiment of using a combination of affinity ligands to generate an indicator from analysis of a sample. Also illustrated is other embodiments in which an amount of sialocomplexes is determined in a sample by an immunoassay according to the present invention. In this illustrative embodiment, a murine anti-human MAG antibody (mAb) was used as the immobilized affinity ligand for binding a component comprising myelin-associated glycoprotein (MAG) in the sample being analyzed. An affinity ligand comprising a detection reagent comprised anti-human antibody, for binding a human antibody component of the sample; or alternatively, comprised an anti-$\alpha$(2,6) NeuAc Ab, for binding a component of the sample comprising a free, terminal alpha 2,6-linked sialic acid. In this illustration, the anti-human antibody comprised either anti-human IgG or anti-human IgM; and the anti-$\alpha$(2,6)NeuAc Ab comprised anti-sTn mAb. For this illustration, the methodology for the immunoassay was essentially performed as described in Example 1 herein. As illustrated in FIG. 2A, the immunoassay for determining human IgM and MAG showed that the amount of this marker (e.g., comprising sialocomplexes) may be present in amount that differs (an increase) in clinical samples from individuals having a disease condition selected from the group consisting of RRMS, SPMS, and PPMS, as compared to the reference value (FIG. 2A, "Control"). As illustrated in FIG. 2B, the immunoassay for determining human IgG and MAG showed that the amount of this marker (e.g., comprising sialocomplexes) may be present in amount that differs (an increase) in clinical samples from individuals having a disease condition selected from the group consisting of RRMS, and SPMS, as compared to the reference value (FIG. 2B, "Control"). However, such an increase in amount of this marker (comprising human IgG and MAG) was not observed in samples from an individual having a disease condition comprising PPMS, a slow progressing form of MS. Similarly, as illustrated in FIG. 2C, the immunoassay for MAG and an epitope comprising free terminal alpha 2,6-linked sialic acid showed that the amount of this marker (e.g., comprising sialocomplexes) may be present in amount that differs (an increase) in clinical samples from individuals having a disease condition selected from the group consisting of RRMS, and SPMS, as compared to the reference value (FIG. 2C, "Control"). However, such an increase in an amount of this marker (comprising MAG and free terminal alpha 2,6-linked sialic acid) was not observed in samples from an individual having a disease condition comprising PPMS, a slow progressing form of MS. The results from FIGS. 2A–2C further suggest that (a) a pro-MS immune response, as identified by an increase (as compared to a reference value) in these markers (e.g., such as sialocomplexes) comprising IgG containing-complexes, may be present in individuals having a disease condition selected from the group consisting of RRMS, SPMS, and a combination thereof; (b) that these markers comprise indicators that may be used to stage and distinguish different forms of MS (e.g., PPMS lacks the indicator comprising IgG-containing complexes, and hence, may be distinguished from RRMS and SPMS; SPMS have a higher observed value of this marker than RRMS, a form of MS that typically precedes SPMS); and (c) that a combination of affinity ligands comprising an affinity ligand having binding specificity for MAG in combination with any one of anti-human IgG or anti-α(2,6)NeuAc Ab may be used to generate an indicator of a disease condition selected from the group consisting of RRMS, SPMS, a pro-MS immune response, or a combination thereof (i.e., RRMS and a pro-MS immune response, or SPMS and a pro-MS immune response).

EXAMPLE 3

Figure 3A:
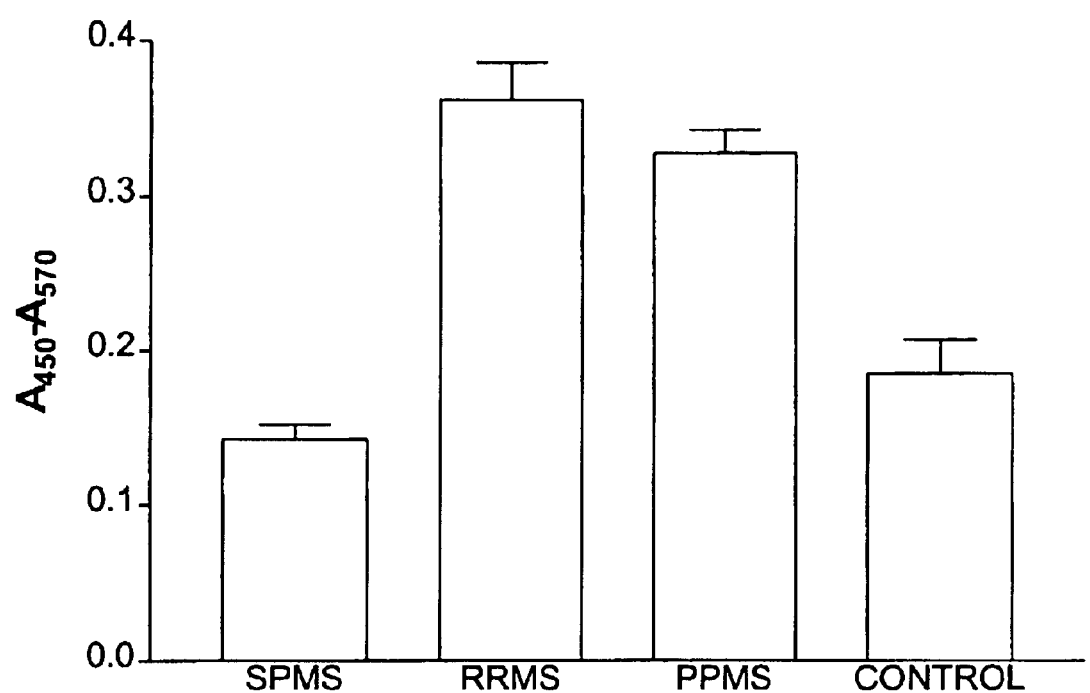
FIG. 3A is a graph illustrating the use of a combination of affinity ligands comprising anti-CD22 mAb and anti-human IgM to generate an indicator for a disease condition selected from the group consisting of MS, a pro-MS immune response, and a combination thereof.
Figure 3B:
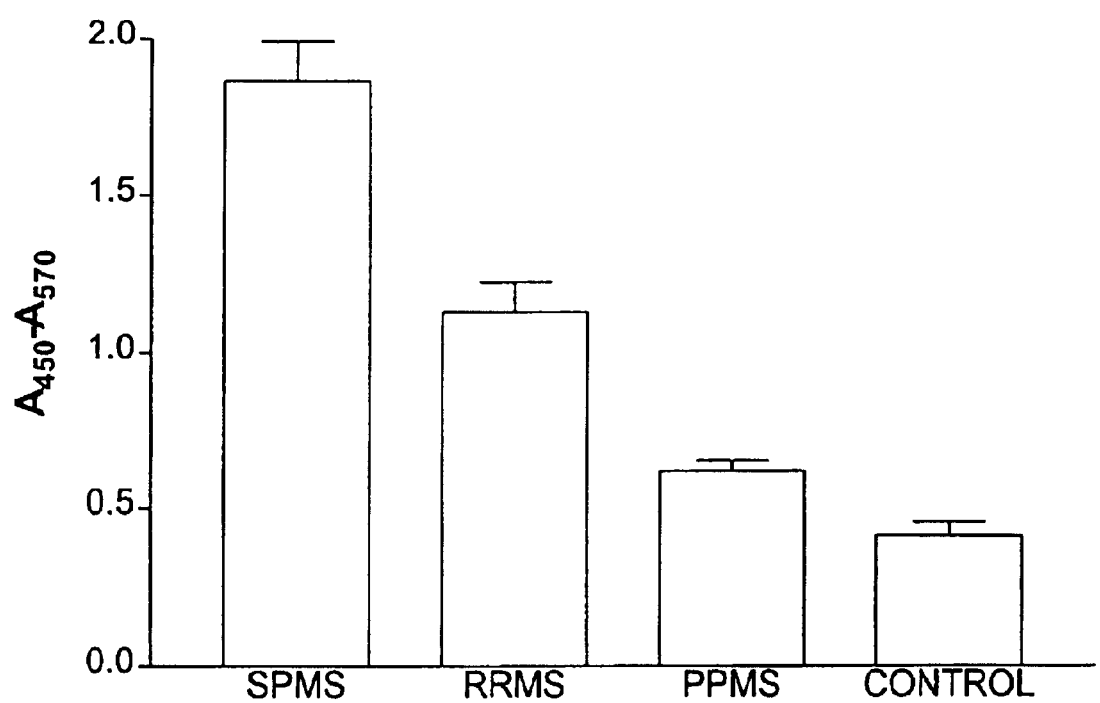
FIG. 3B is a graph illustrating the use of a combination of affinity ligands comprising anti-CD22 mAb and anti-human IgG to generate an indicator for a disease condition selected from the group consisting of MS, a pro-MS immune response, and a combination thereof.
Figure 3C:
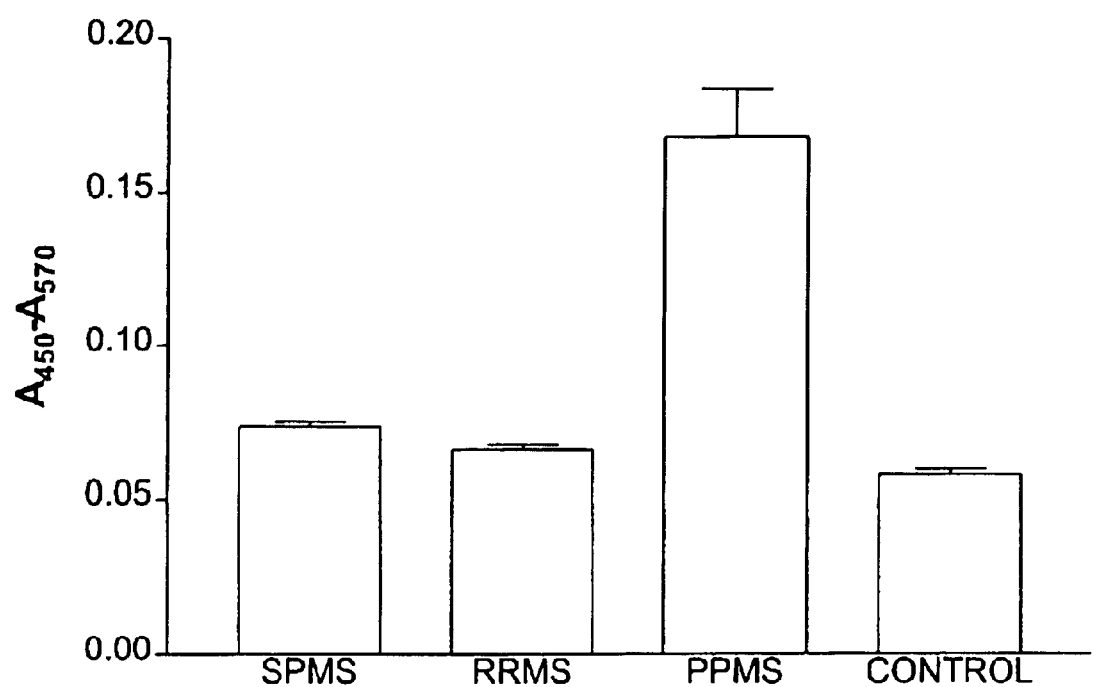
FIG. 3C is a graph illustrating the use of a combination of affinity ligands comprising anti-CD22 mAb and anti-α(2,6) NeuAc Ab to generate an indicator for a disease condition selected from the group consisting of MS, a pro-MS immune response, and a combination thereof.
Figure 3D:
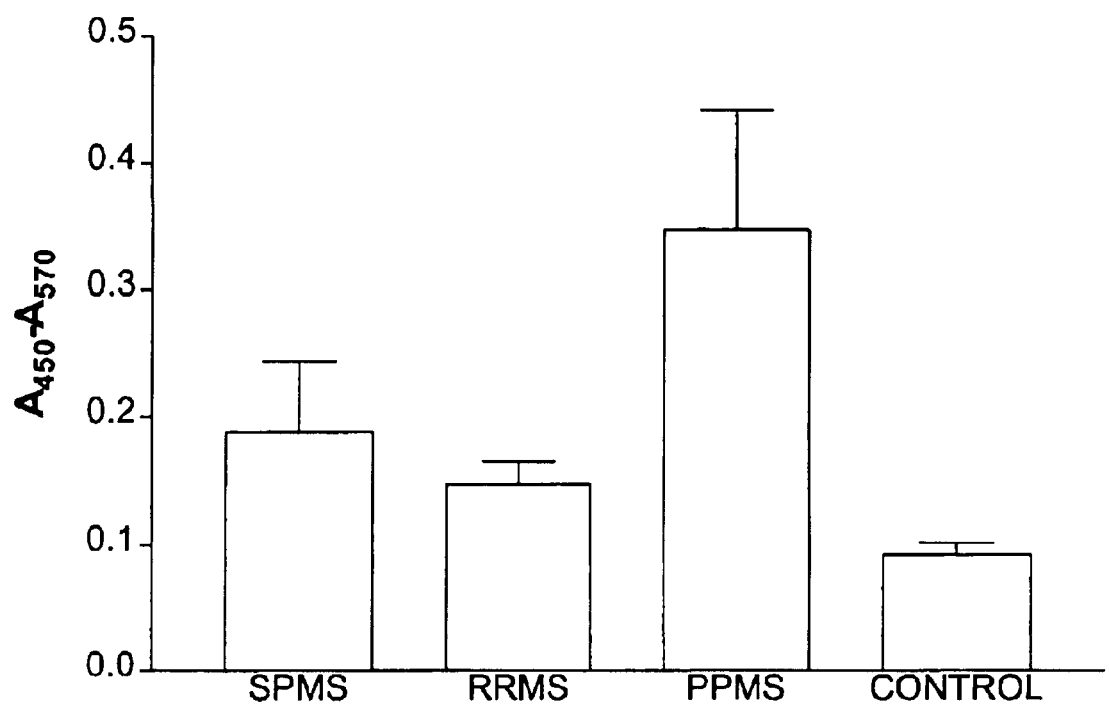
FIG. 3D is a graph illustrating the use of a combination of affinity ligands comprising anti-sTn mAb and anti-CD22 mAb to generate an indicator for a disease condition selected from the group consisting of MS, a pro-MS immune response, and a combination thereof.

This example illustrates another embodiment of using a combination of affinity ligands to generate an indicator from analysis of a sample. Also illustrated are other embodiments wherein an amount of sialocomplexes is determined in a sample by an immunoassay according to the present invention. In this illustrative embodiment, murine anti-human CD22 antibody was used as an immobilized affinity ligand for binding a CD22 component of the sample. The affinity ligand comprising the detection reagent comprised anti-human antibody, for binding a human antibody component of the sample. Alternatively, anti-α(2,6)NeuAc Ab was used as an immobilized affinity ligand for binding free, terminal alpha 2,6-linked sialic acids of the sample; and the affinity ligand comprising the detection reagent comprised anti-human CD22 antibody (mAb). In this illustration, the anti-human antibody comprised either anti-human IgG or anti-human IgM; and the anti-α(2,6)NeuAc Ab comprised anti-sTn mAb. For this illustration, the methodology for the immunoassay was essentially performed as described in Example 1 herein. As illustrated in FIG. 3A, the immunoassay for human IgM and CD22 showed that the amount of this marker (e.g., an amount of sialocomplexes) may be present in amount that differs (an increase) in clinical samples from individuals having a disease condition selected from the group consisting of RRMS, and PPMS, as compared to the amount of the reference value (FIG. 3A, "Control"). As illustrated in FIG. 3B, the immunoassay for human IgG and CD22 showed that the amount of this marker (e.g., an amount of sialocoplexes) may be present in amount that differs (an increase) in clinical samples from individuals having a disease condition selected from the group consisting of RRMS, and SPMS, as compared to the reference value (FIG. 3B, "Control"). However, such an increase in this marker (comprising human IgG and CD22) was not observed in samples from an individual having a disease condition comprising PPMS, a slow progressing form of MS. As illustrated in FIGS. 3C (anti-sTn mAb as the immobilized affinity ligand and anti-CD22 mAb as the detection reagent) and 3D (anti-CD22 mAb as the immobilized affinity ligand and anti-sTn mAb as the detection reagent): a) the marker comprising CD22 and free terminal alpha 2,6-linked sialic acid showed that the amount of this marker (e.g., amount of sialocomplexes) may be present in amount that differs (an increase) in clinical samples from an individual having a disease condition comprising PPMS, as compared to the reference value (FIG. 3C, "Control"). A similar pattern to that illustrated in FIGS. 3C & 3D was seen when anti-MAG mAb was used as the immobilized affinity ligand, and anti-CD22 was used as the detection reagent. However, such a significant increase in this marker (comprising CD22 and free terminal alpha 2,6-linked sialic acid; or comprising MAG and CD22) was not observed in clinical samples from individuals having a disease condition selected from the group consisting of SPMS, and RRMS. The results from FIGS. 3A–3D further suggest that (a) a pro-MS immune response, as identified by an increase (as compared to a reference value) in these markers (e.g., sialocomplexes) comprising IgG containing-immune complexes, may be present in individuals having a disease condition selected from the group consisting of RRMS, and SPMS; (b) that different forms or stages of MS may be distinguishable by these markers individually or as a panel of markers; and (c) that a combination of affinity ligands comprising an affinity ligand having binding specificity for CD22, and anti-human IgG may be used to generate an indicator of a disease condition selected from the group consisting of RRMS, SPMS, a pro-MS immune response, and a combination thereof (i.e., RRMS and a pro-MS immune response, or SPMS and a pro-MS immune response). Thus, an indicator of the presence of a disease condition selected from the group consisting of MS, a pro-MS immune response, and a combination thereof, may comprise an indicator comprising an amount of IgG-containing complexes which differs (e.g., significantly increased), as compared to the reference value.

EXAMPLE 4

In this embodiment, provided are various illustrations of the methods according to the present invention. As illustrated in Examples 1–3 herein, preferred combinations of two affinity ligands which may be used in these methods include one or more of: anti-α(2,6)NeuAc Ab and anti-human IgG mAb; anti-sTn mAb and anti-human IgG mAb; anti-human MAG mAb and anti-human IgM mAb; anti-human MAG mAb and anti-human IgG mAb; anti-human MAG mAb and anti-α(2,6)NeuAc Ab; anti-human MAG mAb and anti-sTn mAb; anti-human MAG mAb and anti-human CD22 mAb; anti-human CD22 mAb and anti-human IgM mAb; anti-human CD22 mAb and anti-human IgG mAb; anti-human CD22 mAb and anti-α(2,6) NeuAc Ab; anti-human CD22 mAb and anti-sTn mAb; and anti-sTn mAb and anti-human CD22 mAb. Thus, an indicator is generated by use in an immunoassay of a combination of affinity ligands according to the present invention, or by use in an immunoassay of more than one combination of affinity ligands. Preferred combinations of affinity ligands may be used to generate individual indicators or a panel of indicators which may be used in diagnostics or prognostics. For example, and as shown in either FIG. 3C or FIG. 3D, an indicator generated using a combination of affinity ligands comprising an affinity ligand which binds specifically to CD22, and an affinity ligand which binds specifically to a terminal alpha 2,6-linked sialic acid (e.g., sTn) may be indicative of a disease condition comprising primary progressive MS. As an illustrative example of generating a panel of indicators, one or more indicators generated from using any one combination of two affinity ligands or a plurality of combinations of two affinity ligands comprising anti-sTn mAb and anti-human IgG mAb, anti-human MAG mAb and anti-human IgM mAb, anti-human MAG mAb and anti-human IgG mAb, anti-human MAG mAb and anti-sTn mAb, and anti-human CD22 mAb and anti-human IgG mAb, may be used in a panel with an indicator generated from a combination of affinity ligands comprising anti-CD22 mAb and anti-human IgM to distinguish a disease condition comprising SPMS from a disease condition comprising RRMS.

In a preferred embodiment according to the present invention a preferred body fluid, of which a sample is to be analyzed, comprises a blood component selected from the group consisting of serum, and plasma. Accordingly, provided is a method for assaying a sample of an individual for an indicator of a disease condition selected from the group consisting of MS, a pro-MS immune response, and a combination thereof, the method comprising: (a) admixing an aliquot of sample under biological assay conditions with a combination of two or more affinity ligands, wherein the two or more affinity ligands are selected from the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent; (b) measuring an amount of the detection reagent, if present, which is bound to the sample in determining a-value of a marker in the sample; (c) comparing the value of the marker determined to a comparative reference value; wherein a difference in the value of the marker determined in the sample, when compared to the reference value, comprises an indicator of the presence of the disease condition. As apparent to those skilled in the art, the sample analyzed, and sample from which the comparative value was determined, should comprise the same body fluid type (i.e., values of a serum marker should be compared to a reference value determined from assay of sera).

In another preferred embodiment, provided is a method for assaying a sample of an individual for monitoring the course of a disease condition selected from the group consisting of MS, a pro-MS immune response, and a combination thereof, the method comprising: (a) admixing an aliquot of sample under biological assay conditions with a combination of two or more affinity ligands, wherein the two or more affinity ligands are selected from the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent; (b) measuring an amount of the detection reagent, if present, which is bound to the sample, in determining a value of a marker in the sample; (c) comparing the value of the marker determined to a comparative value selected from the group consisting of a reference value, a baseline value, and a combination thereof; wherein a difference in the value of the marker determined in the sample, when compared to the comparative value, comprises an indicator of a change in course of the disease condition. This method may be used in a prognostic manner (e.g., the sample analyzed and sample from which the baseline value was measured comprise samples obtained at different points of time relative to the individual); or for monitoring (during or after treatment of the individual's disease) the effect, if any, of treatment on the course of the disease condition; or for predicting whether a particular therapeutic agent (e.g., drug, immunotherapeutic, or the like) can effectively reduce or stabilize the course of the disease condition.

For example, if the individual having a disease condition comprising either SPMS and PMSIR, or RRMS and PMSIR, is undergoing treatment to reduce or suppress the pathology associated with the underlying disease condition, and such treatment is efficacious, the value of the marker (e.g., representative of the amount of sialocomplexes detected by a combination of anti-sTn mAb and anti-human IgG in the sample analyzed after treatment) may show a significant decrease as compared to the baseline value (e.g., representative of the amount of the same type of sialocomplexes from a previous determination). Such a significant decrease may comprise an indicator that the disease condition is being suppressed or reduced, which may also be an indicator of a favorable response to treatment. In another illustrative embodiment, wherein the value of the marker (e.g., representative of the amount of sialocomplexes detected by a combination of anti-MAG mAb and anti-human IgG) is significantly increased as compared to the baseline value (e.g., representative of the amount of the same type of sialocomplexes from a previous determination), such a significant increase may comprise an indicator that the disease condition is progressing in course (e.g., an induction of a more inflammatory disease process underlying the disease condition), which may also be an indicator of an unfavorable prognosis. Such indicators resulting from the methods according to the present invention (e.g., prognostic or diagnostic), is provided as an additional parameter to a competent health professional in making a medical opinion. As will be apparent to those skilled in the art, the comparative values may vary depending upon such factors which include, but are not limited to, the type of clinical sample analyzed (e.g., origin or type of body fluid), the nature of the one or more detection reagents used (binding specificity, detectable moiety, etc.), and the process and instrumentation used to detect the bound detection reagent according to the present invention.

In a similar embodiment of the present invention, provided is a method for assaying a sample of body fluid from an individual for sialocomplexes, the method comprising: (a) admixing an aliquot of the sample under biological assay conditions with a combination of two or more affinity ligands, wherein the two or more affinity ligands are selected from the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent; and (b) measuring an amount of the detection reagent which is bound to sialocomplexes, if present, in determining an amount of the sialocomplexes. The method may further comprise comparing the amount of sialocomplexes determined in the sample to a comparative value for the sialocomplexes, wherein the comparative value is selected from the group consisting of a reference value, a baseline value, and a combination thereof; wherein a difference in the amount of the sialocomplexes determined in the sample, when compared to the comparative value, comprises an indicator of a disease condition selected from the group consisting of MS, a pro-MS immune response, and a combination thereof. In a more preferred embodiment, the sample analyzed comprises serum or plasma. As previously described herein in more detail, the indicator may be used by itself, or in combination with other indicators generated from the sample in forming a panel of indicators, in a diagnostic manner (e.g., when compared to a reference value), prognostic manner (e.g., when compared to a baseline value and/or a reference value), or for monitoring the course of the disease condition (e.g., when compared to a baseline value), in providing an additional parameter to a competent health professional in making a medical opinion.

EXAMPLE 5

The present invention also provides for: (a) removing sialocomplexes from the blood of an individual having a disease process selected from the group consisting of MS, a pro-MS immune response, and a combination thereof, wherein the process for removing the sialocomplexes may be achieved by plasma exchange as known to those skilled in the art of treating autoimmune disorders such as multiple sclerosis; and (b) isolated and purified sialocomplexes that may be isolated and purified from one or more body fluids of an individual having having a disease process selected from the group consisting of MS, a pro-MS immune response, and a combination thereof MS. It will be apparent to one skilled in the art from the descriptions herein that the novel sialocomplexes may be isolated and purified from a body fluid containing the sialocomplexes. In one illustration of this embodiment, peripheral blood was collected from a patient having SPMS and a pro-MS immune response, the blood was heparanized and centrifuged, and the plasma was harvested. The plasma was incubated under biological assay conditions with an affinity column comprising a matrix having immobilized thereto (using methods known on the art of affinity chromatography) one or more affinity ligands having binding specificity for the sialocomplexes. In a preferred embodiment, the affinity ligand immobilized to the affinity matrix comprised one or more of: an anti-anti-α(2, 6)NeuAc Ab; and at least one antibody against at least one member of the sialoadhesin family. In a more preferred embodiment, the affinity ligand immobilized to the matrix is selected from the group consisting of anti-sTn mAb, anti-human MAG mAb, anti-human CD22 mAb, and a combination thereof. In illustrating this embodiment, an anti-sTn mAb was used as the immobilized affinity ligand in the affinity matrix. The affinity matrix comprised commercially available, activated beads (SEPHAROSE™) to which affinity ligand was immobilized according to the manufacturer's instructions. The column was equilibrated with a physiological buffer, and the plasma was then loaded onto, and chromatographed through the column. The treated plasma (i.e., after being passed through the affinity column) was substantially free of detectable sialocomplexes comprising free sTn as determined by assaying a sample of the treated plasma in an immunoassay according to the present invention. In a plasma exchange procedure, the treated plasma may then be directed back into the individual using methods and instruments known to those skilled in the art of plasma exchange.

To isolate and purify the sialocomplexes bound to immobilized affinity ligand in the affinity column, the column was washed with buffer to remove any unbound plasma components, and then the sialocomplexes were eluted from the column using an elution buffer (e.g., 50 mM diethylamine pH 11.5, with 0.1% detergent (SDS)) for a sufficient time to elute the sialocomplexes, resulting in a preparation of isolated and purified sialocomplexes. Various other elution buffers and conditions will be apparent to those skilled in the art from the descriptions herein. If desired, the eluate may be extracted with a mixture of chloroform and methanol, or otherwise treated using methods known to those skilled in the art, to separate the glycolipid component of the sialocomplexes from other components of the sialocomplexes (e.g., one or more sialoadhesin family members). Analysis of the isolated and purified sialocomplexes was performed by polyacrylamide gel electrophoresis under non-reducing conditions, followed by Western Blot analysis. For example, anti-human MAG mAb and anti-sTn mAb were used separately as detection reagents (with a conjugate comprising anti-murine IgG labeled with horseradish peroxidase and a color development reagent comprising DAB) to detect the sialocomplexes, wherein each detector molecule detected the same band comprising the isolated and purified sialocomplexes. High performance thin layer chromatography using a solvent system of chloroform: methanol:0.02% calcium chloride (55:45:10) with 0.002% (w/v) of acridine orange to stain glycolipid was used to show the presence of the glycolipid component of the isolated and purified sialocomplexes.

The isolated and purified sialocomplexes may be used in a number of applications. For example, and as apparent from the descriptions herein of immunoassay formats, the isolated and purified sialocomplexes may be bound to a solid support in forming a solid phase into which is added a clinical sample to detect antibody or a soluble sialoadhesin family member having binding specificity for sialocomplexes that may be present in the clinical sample. Alternatively, the isolated and purified sialocomplexes may be used as an immunizing antigen to generate anti-sialocomplexes antibodies (monoclonal or polyclonal) utilizing standard techniques known in the art. Such antibodies may be useful in an immunoassy format for detecting sialocomplexes, and may be useful in an immunoaffinity procedure to isolate and purify sialocomplexes. More preferably, the isolated and purified sialocomplexes may be quantitated, aliquoted in known amounts, and packaged as a reference standard comprising a known amount of sialocomplexes in the assay kit according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method for assaying a sample of an individual for the indicator of a disease condition selected from the group consisting of MS, a pro-MS immune response, and a combination thereof, the method comprising:
 (a) admixing an aliquot of sample under biological assay conditions with a combination of two or more affinity ligands, wherein the two or more affinity ligands are selected form the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent;

(b) measuring an amount of the detection reagent, if present, which is bound to the sample in determining a value of a marker in the sample;

(c) comparing the value of the marker determined to a comparative reference value;

wherein a difference in the value of the marker determined in the sample, when compared to the reference value, comprises an indicator of the presence of the disease condition.

2. The method according to claim 1, wherein the sample is selected from the group consisting of plasma, and serum.

3. The method according to claim 1, wherein at least one of the affinity ligands comprising the detection reagent further comprises a detectable moiety.

4. The method according to claim 1, wherein at least one of the affinity ligands comprises an affinity ligand immobilized to a solid phase.

5. The method according to claim 1, wherein the anti-human antibody is selected from the group consisting of an anti-human IgG, mAb, an anti-human IgM mAb, and a combination thereof.

6. The method according to claim 1, wherein the affinity ligand having binding specificity for an epitope comprising a terminal alpha 2,6-linked sialic acid comprises an anti-sTn mAb.

7. The method according to claim 1, wherein the affinity ligand having binding specificity for a member of the sialoadhesin family comprises an affinity ligand selected from the group consisting of an anti-human MAG mAb, an anti-CD22 mAb, and a combination thereof.

8. The method according to claim 1, wherein the combination of two or more affinity ligands is a combination selected from the group consisting of anti-α(2,6) NeuAc Ab and an anti-human IgG mAb, anti-sTn mAb and anti-human IgG mAb, anti-human MAG mAb and anti-human IgM mAb, anti-human MAG mAb and anti-human IgG mAb, anti-human MAG mAb and anti-α(2,6) NeuAc Ab, anti-human MAG mAb and anti-sTn mAb, anti-human MAG mAb and anti-human CD22 mAb, anti-human CD22 mAb and anti-human IgM mAb, anti-human CD22 mAb and anti-human IgG mAb, anti-human CD22 mAb and anti-α (2,6) NeuAc Ab, anti-human CD22 mAb and anti-sTn mAb, and a combination thereof.

9. A method for assaying a sample of an individual for monitoring the course of a disease condition selected from the group consisting of MS, a pro-MS immune response, and a combination thereof, the method comprising:

(a) admixing an aliquot of sample under biological assay conditions with a combination of two or more affinity ligands, wherein the two or more affinity ligands are selected from the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent;

(b) measuring an amount of the detection reagent, if present, which is bound to the sample, in determining a value of a marker in the sample;

(c) comparing the value of the marker determined to a comparative value selected from the group consisting of a reference value, a baseline value, and a combination thereof;

wherein a difference in the value of the marker determined in the sample, when compared to the comparative value, comprises an indicator of a change in course of the disease condition.

10. The method according to claim 9, wherein an indicator generated from the method may be used in a process selected from the group consisting of prognostically, for monitoring any effect of treatment on the course of the disease condition, and or for predicting a response of the disease condition to a therapeutic agent.

11. The method according to claim 9, wherein the sample is selected from the group consisting of plasma, and serum.

12. The method according to claim 9, wherein at least one of the affinity ligands comprising the detection reagent further comprises a detectable moiety.

13. The method according to claim 9, wherein at least one of the affinity ligands comprises an affinity ligand immobilized to a solid phase.

14. The method according to claim 9, wherein the anti-human antibody is selected from the group consisting of an anti-human IgG mAb, an anti-human IgM mAb, and a combination thereof.

15. The method according to claim 9, wherein the affinity ligand having binding specificity for an epitope comprising a terminal alpha 2,6-linked sialic acid comprises an anti-sTn mAb.

16. The method according to claim 9, wherein the affinity ligand having binding specificity for a member of the sialoadhesin family comprises an affinity ligand selected from the group consisting of an anti-human MAG mAb, an anti-CD22 mAb, and a combination thereof.

17. The method according to claim 9, wherein the combination of two or more affinity ligands is a combination selected from the group consisting of anti-α(2,6) NeuAc Ab and an anti-human IgG mAb, anti-sTn mAb and anti-human IgG mAb, anti-human MAG mAb and anti-human IgM mAb, anti-human MAG mAb and anti-human IgG mAb, anti-human MAG mAb and anti-α(2,6) NeuAc Ab, anti-human MAG mAb and anti-sTn mAb, anti-human MAG mAb and anti-human CD22 mAb, anti-human CD22 mAb and anti-human IgM mAb, anti-human CD22 mAb and anti-human IgG mAb, anti-human CD22 mAb and anti-α (2,6) NeuAc Ab, anti-human CD22 mAb and anti-sTn mAb, and a combination thereof.

18. A method for assaying a sample of body fluid from an individual for sialocomplexes, the method comprising:

(a) admixing an aliquot of the sample under biological assay conditions with a combination of two our more affinity ligands, wherein the two or more affinity ligands are selected from the group consisting of an anti-human antibody, an affinity ligand having binding specificity for a sialoadhesin family member, and an affinity ligand having binding specificity for an epitope comprising a terminal alpha 2,6-linked sialic acid, and wherein at least one of the affinity ligands comprises a detection reagent; and (b) and measuring an amount of the detection reagent which is bound to sialocomplexes, if present, in determining an amount of the sialocomplexes.

19. The method according to claim 18, further comprising comparing the amount of sialocomplexes determined in the sample to a comparative value for the sialocomplexes, wherein the comparative value is selected from the group consisting of a reference value, a baseline value, and a combination thereof; wherein a difference in the amount of the sialocomplexes determined in the sample, when compared to the comparative value, comprises an indicator of a disease condition selected from the group consisting of MS, a pro-MS immune response, and a combination thereof.

20. The method according to claim 19, wherein an indicator generated from the method may be used in a process selected from the group consisting of prognostically, for monitoring any effect of treatment on the course of the of the disease condition, and or for predicting a response of the disease condition to a therapeutic agent.

21. The method according to claim 18, wherein the sample is selected from the group consisting of plasma, and serum.

22. The method according to claim 18, wherein at least one of the affinity ligands comprising the detection reagent further comprises a detectable moiety.

23. The method according to claim 18, wherein at least one of the affinity ligands comprises an affinity ligand immobilized to a solid phase.

24. The method according to claim 18, wherein the anti-human antibody is selected from the group consisting of an anti-human IgG mAb, an anti-human IgM mAb, and a combination thereof.

25. The method according to claim 18, wherein the affinity ligand having binding specificity for an epitope comprising a terminal alpha 2,6-linked sialic acid comprises an anti-sTn mAb.

26. The method according to claim 18, wherein the affinity ligand having binding specificity for a member of the sialoadhesin family comprises an affinity ligand selected from the group consisting of an anti-human MAG mAb, an anti-CD22 mAb, and a combination thereof.

27. The method according to claim 19, wherein the combination of two or more affinity ligands is a combination selected from the group consisting of anti-α(2,6) NeuAc Ab and an anti-human IgG mAb, anti-sTn mAb and anti-human IgG mAb, anti-human MAG mAb and anti-human IgM mAb, anti-human MAG mAb and anti-human IgG mAb, anti-human MAG mAb and anti-α (2,6) NeuAc Ab, anti-human MAG mAb and anti-sTn mAb, anti-human MAG mAb and anti-human CD22 mAb, anti-human CD22 mAb and anti-human IgM mAb, anti-human CD22 mAb and anti-human IgG mAb, anti-human CD22 mAb and anti-α (2,6) NeuAc Ab, anti-human CD22 mAb and anti-sTn mAb, and a combination thereof.

28. A method comprising:
(a) admixing an aliquot of sample under biological assay conditions with a combination of two or more affinity ligands, wherein the affinity ligands are selected from the group consisting of an anti-human antibody, an affinity ligand having binding specificity for a sialoadhesin family member, and an affinity ligand having binding specificity for an epitope comprising a terminal a 2,6-linked sialic acid, and wherein at least one of the affinity ligands comprises a detection reagent;
(b) measuring an amount of the detection reagent which is bound to the sample to determine a value of a marker in the sample;
(c) comparing the value of the marker in the sample to a comparative reference value;
wherein the comparing indicates the presence or absence of a disease condition.

29. The method according to claim 28, wherein the sample is selected from the group consisting of plasma, and serum.

30. The method according to claim 28, wherein at least one of the affinity ligands comprising the detection reagent further comprises a detectable moiety.

31. The method according to claim 28, wherein at least one of the affinity ligands comprises an affinity ligand immobilized to a solid phase.

32. The method according to claim 28, wherein the anti-human antibody is selected from the group consisting of an anti-human IgG mAb, an anti-human IgM mAb, and a combination thereof.

33. The method according to claim 28, wherein the affinity ligand having binding specificity for an epitope comprising a terminal α 2,6-linked sialic acid comprises an anti-sTn mAb.

34. The method according to claim 28, wherein the affinity ligand having binding specificity for a member of the sialoadhesin family comprises an affinity ligand selected from the group consisting of an anti-human MAG mAb, an anti-CD22 mAb, and a combination thereof.

35. The method according to claim 28, wherein the combination of two or more affinity ligands is a combination selected from the group consisting of anti-α(2,6) NeuAc Ab and an anti-human IgG mAb, anti-sTn mAb and anti-human IgG mAb, anti-human MAG mAb and anti-human IgM mAb, anti-human MAG mAb and anti-human IgG mAb, anti-human MAG mAb and anti-α(2,6) NeuAc Ab, anti-human MAG mAb and anti-sTn mAb, anti-human MAG mAb and anti-human CD22mAb, anti-human CD22 mAb and anti-human IgM mAb, anti-human CD22 mAb and anti-human IgG mAb, anti-human CD22 mAb and anti-α (2,6) NeuAc Ab, anti-human CD22 mAb and anti-sTn mAb, and a combination thereof.

36. A method comprising:
(a) admixing an aliquot of sample under biological assay conditions with a combination of two or more affinity ligands, wherein the affinity ligands are selected from the group consisting of an anti-human antibody, an affinity ligand having binding specificity for a sialoadhesin family member, and an affinity ligand having binding specificity for an epitope comprising a terminal a 2,6-linked sialic acid, and wherein at least one of the affinity ligands comprises a detection reagent;
(b) determining a level of the detection reagent which is bound to the sample;
(c) comparing the level of the detection reagent to a comparative reference;
(d) deriving an indicator for the presence or absence of a disease condition selected form the group consisting of MS, a pro-MS immune response, and a combination thereof based on the comparing.

37. The method according to claim 36, wherein the indicator may be used in a process selected from the group consisting of prognostically, for monitoring any effect of treatment on the course of the disease condition, and or for predicting a response of the disease condition to a therapeutic agent.

38. The method according to claim 36, wherein the sample is selected from the group consisting of plasma, and serum.

39. The method according to claim 36, wherein at least one of the affinity ligands comprising the detection reagent further comprises a detectable moiety.

40. The method according to claim 36, wherein at least one of the affinity ligands comprises an affinity ligand immobilized to a solid phase.

41. The method according to claim 36, wherein the anti-human antibody is selected from the group consisting of an anti-human IgG mAb, an anti-human IgM mAb, and a combination thereof.

42. The method according to claim 36, wherein the affinity ligand having binding specificity for an epitope comprising a terminal α2,6-linked sialic acid comprises an anti-sTn mAb.

43. The method according to claim 36, wherein the affinity ligand having binding specificity for a member of the sialoadhesin family comprises an affinity ligand selected from the group consisting of an anti-human MAG mAb, an anti-CD22 mAb, and a combination thereof.

44. The method according to claim 36, wherein the combination of two or more affinity ligands is a combination selected from the group consisting of anti-α(2,6) NeuAc Ab and an anti-human IgG mAb, anti-sTn mAb and anti-human IgG mAb, anti-human MAG mAb and anti-human IgM mAb, anti-human MAG mAb and anti-human IgG mAb, anti-human MAG mAb and anti-α(2,6) NeuAc Ab, anti-human MAG mAb and anti-sTn mAb, anti-human MAG mAb and anti-human CD22mAb, anti-human CD22 mAb and anti-human IgM mAb, anti-human CD22 mAb and anti-human IgG mAb, anti-human CD22 mAb and anti-α(2,6) NeuAc Ab, anti-human CD22 mAb and anti-sTn mAb, and a combination thereof.

* * * * *